(12) United States Patent
Yoo et al.

(10) Patent No.: US 8,742,104 B2
(45) Date of Patent: Jun. 3, 2014

(54) SATURATED N-HETEROCYCLIC CARBENE-LIGAND METAL COMPLEX DERIVATIVES, PREPARING METHOD THEREOF, AND PREPARING METHOD OF SILANE COMPOUND BY HYDROSILYLATION REACTION USING THE SAME AS CATALYST

(75) Inventors: Bok Ryul Yoo, Seoul (KR); Joon Soo Han, Gyeonggi-do (KR); Jang Hyun Yoo, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 373 days.

(21) Appl. No.: 12/846,554

(22) Filed: Jul. 29, 2010

(65) Prior Publication Data

US 2011/0160454 A1     Jun. 30, 2011

(51) Int. Cl.
| | |
|---|---|
| *C07F 15/00* | (2006.01) |
| *C08G 77/08* | (2006.01) |
| *C07D 233/02* | (2006.01) |
| *C07D 239/04* | (2006.01) |
| *C07F 15/04* | (2006.01) |

(52) U.S. Cl.
CPC ............. *C07F 15/00* (2013.01); *C07F 15/0006* (2013.01); *C07F 15/04* (2013.01); *C08G 77/08* (2013.01); *C07D 233/02* (2013.01); *C07D 239/04* (2013.01)
USPC .......................................... 544/225; 548/103

(58) Field of Classification Search
CPC ...... C07F 15/00; C07F 15/0006; C07F 15/04; C08G 77/08; C07D 233/02; C07D 239/04
USPC ........................................... 548/103; 544/225
See application file for complete search history.

(56) References Cited

U.S. PATENT DOCUMENTS

| | | | |
|---|---|---|---|
| 2,823,218 A | 2/1958 | Speier et al. | |
| 2,970,150 A | 1/1961 | Bailey | |
| 3,775,452 A | 11/1973 | Karstedt | |

FOREIGN PATENT DOCUMENTS

| | | |
|---|---|---|
| KR | 10-2002-0059446 A | 7/2002 |
| KR | 10-0595948 B | 7/2006 |
| WO | WO 01/42258 A | 6/2001 |

OTHER PUBLICATIONS

Speier, John L. et al.: "The Addition of Silicon Hydrides to OlefinicDouble Bonds. Part II. The Use of Group VIII Metal Catalysts", *J.Am.Chem.Soc.*, 1957, 79, pp. 974-979.

Berthon-Gelloz, Guillaume et al.: "Synthetic and structural studies of NHC-Pt(dvtms) complexes and their application as alkene hydrosilylation catalysts (NHC = N-heterocyclic carbine, dvtms=divinyltetramethylsiloxane)", Journal of Organometallic Chemistry, 690 (2005), pp. 6156-6168.

*Primary Examiner* — Deepak Rao
(74) *Attorney, Agent, or Firm* — Frommer Lawrence & Haug LLP; Ronald R Santucci

(57) ABSTRACT

Provided are a saturated N-heterocyclic carbene-ligand metal complex derivative, a method for preparing the same, and a method for preparing a silane compound by hydrosilylation using the same as a catalyst. To describe in more detail, the metal complex derivative has a saturated N-heterocyclic carbene derivative and an olefin ligand at the same time. A silane compound is prepared by hydrosilylation in the presence of the metal complex derivative as a catalyst. The provided metal complex derivative of the present invention has superior stability during hydrosilylation reaction and is capable of effectively performing the hydrosilylation reaction at low temperature even with small quantity. Further, a product with superior regioselectivity may be obtained. In addition, after the hydrosilylation reaction is completed, the metal complex derivative may be recovered and recycled.

16 Claims, No Drawings

SATURATED N-HETEROCYCLIC CARBENE-LIGAND METAL COMPLEX DERIVATIVES, PREPARING METHOD THEREOF, AND PREPARING METHOD OF SILANE COMPOUND BY HYDROSILYLATION REACTION USING THE SAME AS CATALYST

CROSS-REFERENCE TO RELATED APPLICATIONS

This application claims under 35 U.S.C. §119(a) the benefit of Korean Patent Application No. 10-2009-0135387 filed Dec. 31, 2009, the entire contents of which are incorporated herein by reference.

TECHNICAL FIELD

The present invention relates to a metal complex derivative having a saturated N-heterocyclic carbene derivative and an olefin ligand at the same time and a method for preparing the same. The present invention also relates to a method for preparing a silane compound by hydrosilylation reaction using the metal complex derivative as a catalyst.

BACKGROUND ART

Organosilicon compounds are produced by formation of Si—C bonds. Especially, hydrosilylation describes the addition reaction between an organosilicon compound having a Si—H bond and an unsaturated hydrocarbon such as olefin or acetylene derivatives. Typically, the reaction is performed in the presence of a metal catalyst. A hydrosilylation reaction of an olefin may be represented by Scheme 1:

[Scheme 1]

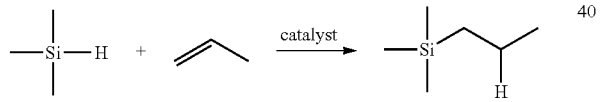

For the metal complex catalyst, group 10 transition metal compounds are known to be effective for the hydrosilylation reaction. In particular, platinum-based compounds are industrially widely used as catalyst. Historically, chloroplatinic acid ($H_2PtCl_6/^iPrOH$) was first known to be an effective catalyst in the hydrosilylation reaction in 1957 [Speier, J. L. and Hook, D. E. U.S. Pat. No. 2,823,218 (1958); Speier, John L., Webster, James A. and Barnes, Garrett H. *J. Am. Chem. Soc.* 1957, 79, 974-9]. Bailey, D. L. and Snyder, N.Y. reported catalytic activity of platinum supported on alumina (Pt@g-alumina) [U.S. Pat. No. 2,970,150, 1961]. However, the hydrosilylation reaction described in the above US patents is economically unfavorable because a large quantity of platinum catalyst has to be used.

At present, in most industrial-scale preparation of organosilicon compounds by hydrosilylation, the Karstedt catalyst, i.e. a platinum complex in oxidation state 0, is used. The general formula of the Karstedt complex is $Pt_2[(CH_2=CH)Me_2Si—O—SiMe_2(CH=CH_2)]_3$ [Karstedt, B. D., U.S. Pat. No. 3,775,452, 1973]. The Karstedt catalyst has a drawback that it is unstable during hydrosilylation, which can be ascertained by the precipitation of metallic platinum in the reaction medium and the formation of insoluble colloid. The instability of the catalyst in the reaction medium may result in decrease in catalytic activity. Furthermore, the instability of the Karstedt catalyst induces the formation of colored hydrosilylation products, thereby resulting in a cloudy, colored solution. Besides, because of production of byproduct, the Karstedt catalyst gives a low yield from hydrosilylation reaction. In addition to the desired product, byproducts resulting from isomerization and/or hydrogenation of the olefinic double bond are obtained.

In order to solve the problems of the Karstedt catalyst, Marko et al. reported a new catalyst [WO 2001/42,258], which is a metal complex

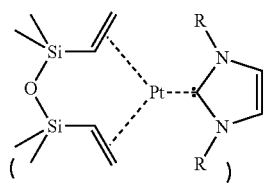

containing an unsaturated 5-membered N-heterocyclic carbene (U-NHC$_5$). The patent restrictively describes hydrosilylation of a hydrosilane ((bissilyloxy)hydrosilane: $Me_3SiO—SiHMe—OSiMe_3$). The hydrosilane is a component of hydrosilicone oil and is widely used in the silicone industry. Although the carbene metal complex catalyst developed by Marko et al. is advantageous in that it is relatively stable under air and the metal complex structure is maintained during storage and hydrosilylation, catalytic activity of hydrosilylation is unsatisfactory.

DISCLOSURE

Technical Problem

The inventors of the present invention, in an effort to develop a method for the effective preparation of silane compounds, have succeeded in synthesizing a metal complex derivative having a saturated N-heterocyclic carbene derivative, not an unsaturated N-heterocyclic carbene, of a specific structure and an olefin ligand of a specific structure at the same time, and found that when the metal complex derivative is used as a catalyst in the preparation of organosilicon compounds, the rate of hydrosilylation reaction and the yield of the silane compound can be improved. Accordingly, an object of the present invention is to provide a saturated N-heterocyclic carbene-ligand metal complex derivative, a method for preparing the same, and a method for preparing a silane compound by hydrosilylation reaction using the same as a catalyst.

Technical Solution

In one general aspect, the present invention provides a saturated N-heterocyclic carbene-ligand metal complex represented by Chemical Formula 1:

(1)

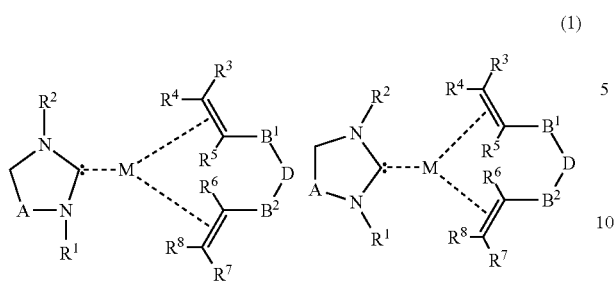

wherein A is

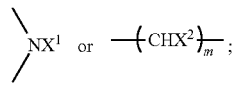

$X^1$, $X^2$, $R^1$ and $R^2$ are identical to or different from one another, and each of $X^1$, $R^1$ and $R^2$ is $C_1$-$C_{18}$ linear or branched alkyl, $C_5$-$C_{18}$ cycloalkyl, $C_3$-$C_{18}$ unsaturated hydrocarbon or $C_6$-$C_{18}$ aryl, and $X^2$ is hydrogen, $C_1$-$C_{18}$ linear or branched alkyl, $C_5$-$C_{18}$ cycloalkyl, $C_3$-$C_{18}$ unsaturated hydrocarbon or $C_6$-$C_{18}$ aryl; M is a group 10 transition metal in the periodic table with oxidation state 0; m is an integer from 1 to 4; $B^1$ and $B^2$ are identical to or different from each other, and each of $B^1$ and $B^2$ is

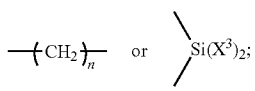

$X^3$ is $C_1$-$C_{18}$ linear or branched alkyl, $C_5$-$C_{18}$ cycloalkyl, $C_3$-$C_{18}$ unsaturated hydrocarbon or $C_6$-$C_{18}$ aryl; n is an integer from 1 to 4; D is oxygen,

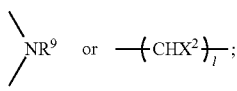

l is an integer from 1 to 4; and $R^3$, $R^4$, $R^5$, $R^6$, $R^7$, $R^8$ and $R^9$ are identical to or different from one another, and each of $R^3$, $R^4$, $R^5$, $R^6$, $R^7$, $R^8$ and $R^9$ is hydrogen, $C_1$-$C_{18}$ linear or branched alkyl, $C_5$-$C_{18}$ cycloalkyl, $C_3$-$C_{18}$ unsaturated hydrocarbon or $C_6$-$C_{18}$ aryl.

In another general aspect, the present invention provides a method for preparing the saturated N-heterocyclic carbene-ligand metal complex represented by Chemical Formula 1, comprising: reacting an unsaturated olefin ligand represented by Chemical Formula 3 with a group 10 (8B) transition metal in the periodic table with oxidation state 0 to prepare a metal-containing unsaturated olefin ligand; treating a 1,3-diazocycloalk-1-ene salt represented by Chemical Formula 2 with a strong base to prepare a saturated N-heterocyclic carbene; and reacting the saturated N-heterocyclic carbene with the metal-containing unsaturated olefin ligand at 0 to 70° C. in a specific solvent to synthesize a carbene-ligand metal complex derivative:

(2)

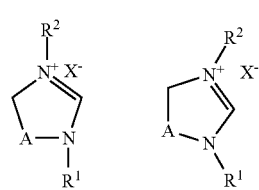

wherein A is

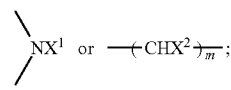

$X^1$, $X^2$, $R^1$ and $R^2$ are identical to or different from one another, and each of $X^1$, $R^1$ and $R^2$ is $C_1$-$C_{18}$ linear or branched alkyl, $C_5$-$C_{18}$ cycloalkyl, $C_3$-$C_{18}$ unsaturated hydrocarbon or $C_6$-$C_{18}$ aryl, and $X^2$ is hydrogen, $C_1$-$C_{18}$ linear or branched alkyl, $C_5$-$C_{18}$ cycloalkyl, $C_3$-$C_{18}$ unsaturated hydrocarbon or $C_6$-$C_{18}$ aryl; m is an integer from 1 to 4; and $X^-$ is an anion derived from an organic or inorganic Brønsted acid, with pKa 0.01 to 6; and (3)

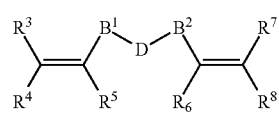

wherein $B^1$ and $B^2$ are identical to or different from each other, and each of $B^1$ and $B^2$ is

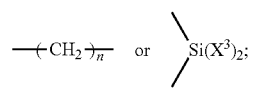

$X^3$ is $C_1$-$C_{18}$ linear or branched alkyl, $C_5$-$C_{18}$ cycloalkyl, $C_3$-$C_{18}$ unsaturated hydrocarbon or $C_6$-$C_{18}$ aryl; n is an integer from 1 to 4; D is oxygen,

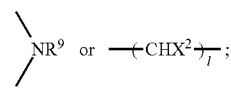

l is an integer from 1 to 4; and $R^3$, $R^4$, $R^5$, $R^6$, $R^7$, $R^8$ and $R^9$ are identical to or different from one another, and each of $R^3$, $R^4$, $R^5$, $R^6$, $R^7$, $R^8$ and $R^9$ is hydrogen, $C_1$-$C_{18}$ linear or branched alkyl, $C_5$-$C_{18}$ cycloalkyl, $C_3$-$C_{18}$ unsaturated hydrocarbon or $C_6$-$C_{18}$ aryl.

In another general aspect, the present invention provides a method for preparing a method for preparing a silane compound by hydrosilylation in the presence of the saturated N-heterocyclic carbene-ligand metal complex derivative.

Advantageous Effects

The metal complex derivative of the present invention has superior stability during hydrosilylation reaction and is capable of effectively performing the hydrosilylation reaction at low temperature even with small quantity. Further, a product with superior regioselectivity may be obtained. In addition, after the hydrosilylation reaction is completed, the metal complex derivative may be recovered and recycled.

BEST MODE

Hereinafter, the embodiments of the present invention will be described in detail.

As used herein, "hydrosilylation reaction" refers to a reaction between a compound having one or more Si—H bonding unit(s) and an olefin (having double bond(s)), an acetylene derivative (having triple bond(s)) or a compound having both double and triple bonds to form C—Si bonds.

The present invention provides a saturated N-heterocyclic carbene-ligand metal complex represented by Chemical Formula 1:

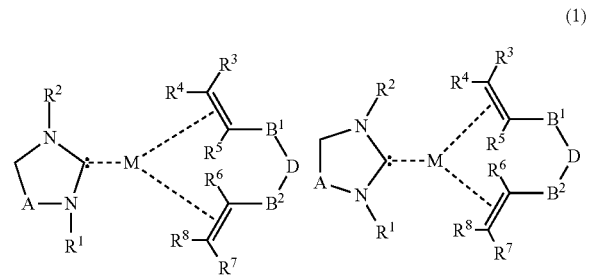

(1)

wherein A is

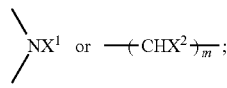

$X^1$, $X^2$, $R^1$ and $R^2$ are identical to or different from one another, and each of $X^1$, $R^1$ and $R^2$ is $C_1$-$C_{18}$ linear or branched alkyl, $C_5$-$C_{18}$ cycloalkyl, $C_3$-$C_{18}$ unsaturated hydrocarbon or $C_6$-$C_{18}$ aryl, and $X^2$ is hydrogen, $C_1$-$C_{18}$ linear or branched alkyl, $C_5$-$C_{18}$ cycloalkyl, $C_3$-$C_{18}$ unsaturated hydrocarbon or $C_6$-$C_{18}$ aryl; M is a group 10 transition metal in the periodic table with oxidation state 0; m is an integer from 1 to 4; $B^1$ and $B^2$ are identical to or different from each other, and each of $B^1$ and $B^2$ is

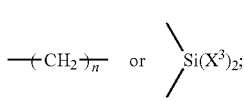

$X^3$ is $C_1$-$C_{18}$ linear or branched alkyl, $C_5$-$C_{18}$ cycloalkyl, $C_3$-$C_{18}$ unsaturated hydrocarbon or $C_6$-$C_{18}$ aryl; n is an integer from 1 to 4; D is oxygen,

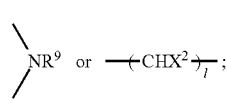

l is an integer from 1 to 4; and $R^3$, $R^4$, $R^5$, $R^6$, $R^7$, $R^8$ and $R^9$ are identical to or different from one another, and each of $R^3$, $R^4$, $R^5$, $R^6$, $R^7$, $R^8$ and $R^9$ is hydrogen, $C_1$-$C_{18}$ linear or branched alkyl, $C_5$-$C_{18}$ cycloalkyl, $C_3$-$C_{18}$ unsaturated hydrocarbon or $C_6$-$C_{18}$ aryl.

Preferably, in Chemical Formula 1, A is

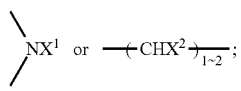

$X^1$, $X^2$, $R^1$ and $R^2$ are identical to or different from one another, and each of $X^1$, $R^1$ and $R^2$ is $C_1$-$C_{10}$ linear or branched alkyl, $C_5$-$C_{10}$ cycloalkyl or $C_6$-$C_{18}$ aryl, $X^2$ is hydrogen, $C_1$-$C_{10}$ alkyl, $C_5$-$C_{10}$ linear or branched alkyl or $C_6$-$C_{18}$ aryl; M is nickel, palladium or platinum; $B^1$ and $B^2$ are identical to or different from each other, and each of $B^1$ and $B^2$ is

$X^3$ is $C_1$-$C_{10}$ linear or branched alkyl, $C_5$-$C_{10}$ cycloalkyl or $C_6$-$C_{18}$ aryl; D is oxygen or

$R^3$ through $R^9$ are identical to or different from one another, and each of $R^3$ through $R^9$ is hydrogen, $C_1$-$C_{10}$ alkyl or $C_6$-$C_{18}$ aryl. More preferably, in Chemical Formula 1, A is

$X^2$ is hydrogen; each of $R^1$ and $R^2$ is $C_1$-$C_5$ linear or branched alkyl or $C_5$-$C_8$ cycloalkyl; M is nickel, palladium or platinum; each of $B^1$ and $B^2$ is

$X^3$ is $C_1$-$C_3$ alkyl; D is oxygen; and each of $R^3$ through $R^8$ is hydrogen.

In the saturated N-heterocyclic carbene ligand metal complex derivative of the present invention, $R^3$ and $R^7$ may form a cyclic ligand represented by Chemical Formula 4:

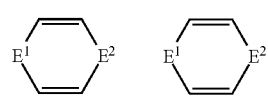

(4)

wherein $E^1$ and $E^2$ are identical to or different from each other, and each of $E^1$ and $E^2$ is

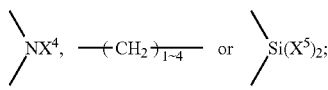

and $X^4$ and $X^5$ are identical to or different from each other, and each of $X^4$ and $X^5$ is $C_1$-$C_{18}$ alkyl or $C_6$-$C_{18}$ aryl.

The saturated N-heterocyclic carbene-ligand metal complex derivative of the present invention is appropriate to be used as a catalyst in hydrosilylation reaction.

Hereinafter, a method for preparing the saturated N-heterocyclic carbene-ligand metal complex derivative of the present invention will be described.

[Preparation of Saturated N-Heterocyclic Carbene-Ligand Metal Complex Derivative]

The present invention provides a method for preparing a saturated N-heterocyclic carbene-ligand metal complex derivative, comprising: reacting an unsaturated olefin ligand represented by Chemical Formula 3 with a group 10 transition metal in the periodic table with oxidation state '0' to prepare a metal-containing unsaturated olefin ligand; treating a 1,3-diazocycloalk-1-ene salt represented by Chemical Formula 2 with a strong base to prepare a saturated N-heterocyclic carbene; and reacting the saturated N-heterocyclic carbene with the metal-containing unsaturated olefin ligand at 0 to 70° C. in a specific solvent to synthesize a carbene-ligand metal complex derivative.

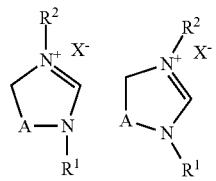

(2)

In Chemical Formula 2, A is

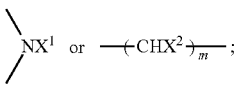

$X^1$, $X^2$, $R^1$ and $R^2$ are identical to or different from one another, and each of $X^1$, $R^1$ and $R^2$ is $C_1$-$C_{18}$ linear or branched alkyl, $C_5$-$C_{18}$ cycloalkyl, $C_3$-$C_{18}$ unsaturated hydrocarbon or $C_6$-$C_{18}$ aryl, and $X^2$ is hydrogen, $C_1$-$C_{18}$ linear or branched alkyl, $C_5$-$C_{18}$ cycloalkyl, $C_3$-$C_{18}$ unsaturated hydrocarbon or $C_6$-$C_{18}$ aryl; m is an integer from 1 to 4; and $X^-$ is an anion derived from an organic or inorganic Brønsted acid, with pKa 0.01 to 6.

Preferably, in Chemical Formula 2, A is

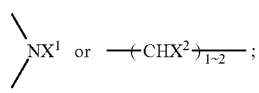

each of $X^1$, $R^1$ and $R^2$ is $C_1$-$C_{10}$ linear or branched alkyl, $C_5$-$C_{10}$ cycloalkyl or $C_6$-$C_{18}$ aryl; and each of $X^2$, $R^1$ and $R^2$ is hydrogen, $C_1$-$C_{10}$ alkyl, $C_5$-$C_{10}$ linear or branched alkyl, $C_5$-$C_{10}$ cycloalkyl or $C_6$-$C_{18}$ aryl. More preferably, in Chemical Formula 2, A is $-\!\!\left(CHX^2\right)_{\overline{1\text{-}2}}\!-\!;$ $X^2$ is hydrogen; and each of $R^1$ and $R^2$ is $C_1$-$C_5$ linear or branched alkyl or $C_5$-$C_8$ cycloalkyl.

The 1,3-diazocycloalk-1-ene salt represented by Chemical Formula 2 may be prepared, for example, according to Scheme 2, without being limited thereto:

[Scheme 2]

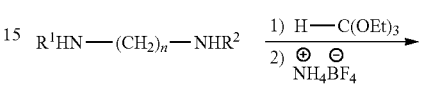

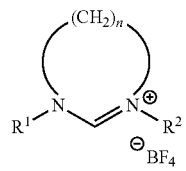

(3)

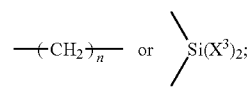

In Chemical Formula 3, $B^1$ and $B^2$ are identical to or different from each other, and each of $B^1$ and $B^2$ is $-\!\!\left(CH_2\right)_{\overline{n}}\!-\!$ or $\phantom{x}\diagdown\!\!Si(X^3)_2;\phantom{x}\diagup$ $X^3$ is $C_1$-$C_{18}$ linear or branched alkyl, $C_5$-$C_{18}$ cycloalkyl, $C_3$-$C_{18}$ unsaturated hydrocarbon or $C_6$-$C_{18}$ aryl; n is an integer from 1 to 4; D is oxygen, $\phantom{x}\diagdown\!\!NR^9\phantom{x}\diagup$ or $-\!\!\left(CHX^2\right)_{\overline{1}}\!-\!;$ l is an integer from 1 to 4; and $R^3$, $R^4$, $R^5$, $R^6$, $R^7$, $R^8$ and $R^9$ are identical to or different from one another, and each of $R^3$, $R^4$, $R^5$, $R^6$, $R^7$, $R^8$ and $R^9$ is hydrogen, $C_1$-$C_{18}$ linear or branched alkyl, $C_5$-$C_{18}$ cycloalkyl, $C_3$-$C_{18}$ unsaturated hydrocarbon or $C_6$-$C_{18}$ aryl. Preferably, in Chemical Formula 3, M is nickel, palladium or platinum; each of $B^1$ and $B^2$ is

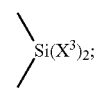

$X^3$ is $C_1$-$C_{10}$ linear or branched alkyl, $C_5$-$C_{10}$ cycloalkyl or $C_6$-$C_{18}$ aryl; D is oxygen or

$R^3$ through $R^9$ are identical to or different from one another, and each of $R^3$ through $R^9$ is hydrogen, $C_1$-$C_{10}$ linear or branched alkyl or $C_6$-$C_{18}$ aryl. More preferably, in Chemical Formula 3, each of $B^1$ and $B^2$ is

$X^3$ is $C_1$-$C_3$ 의 alkyl; D is oxygen; and each of $R^3$ through $R^8$ is hydrogen. Further more preferably, the unsaturated olefin ligand represented by Chemical Formula 3 is

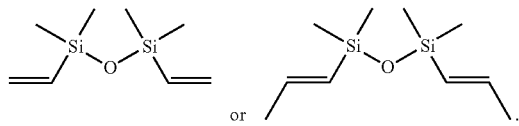

A specific example of the metal-containing unsaturated olefin ligand prepared from the reaction of an unsaturated olefin ligand and a group 10 transition metal is represented by Chemical Formula 5:

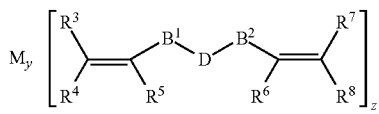

(5)

wherein M is a group 10 transition metal in the periodic table with oxidation state 0; y is an integer from 1 to 3; z is an integer from 1 to 4; $B^1$ and $B^2$ are identical to or different from each other, and each of $B^1$ and $B^2$ is

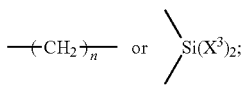

$X^3$ is $C_1$-$C_{18}$ linear or branched alkyl, $C_5$-$C_{18}$ cycloalkyl, $C_3$-$C_{18}$ unsaturated hydrocarbon or $C_6$-$C_{18}$ aryl, n is an integer from 1 to 4; D is oxygen,

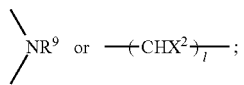

$R^3$ through $R^9$ are identical to or different from one another, and each of $R^3$ through $R^9$ is hydrogen, $C_1$-$C_{18}$ linear or branched alkyl, $C_3$-$C_{18}$ cycloalkyl, $C_3$-$C_{18}$ unsaturated hydrocarbon or $C_6$-$C_{18}$ aryl; and l is an integer from 1 to 4. Preferably, M is nickel, palladium or platinum, more preferably platinum.

When preparing the saturated N-heterocyclic carbene by treating the 1,3-diazocycloalk-1-ene salt with a strong base, the strong base may be one or more selected from alkali metal-containing hydride, hydroxide, carboxylate, alcoholate and amide. More preferably, one or more base selected from NaOH, NaOCH$_3$, KOH, KOCH$_2$(CH$_3$)$_2$, KOCH$_2$(CH$_3$)$_3$ and LiNHCH$_2$(CH$_3$)$_2$ is used. If the starting salt is highly reactive, it is preferred to perform the reaction at low temperature. Accordingly, the treatment with the strong base is performed preferably at 15 to 60° C., more preferably at 15 to 35° C.

Preferably, the reaction between the saturated N-heterocyclic carbene and the metal-containing unsaturated olefin ligand is performed at 0 to 70° C., preferably at 15 to 50° C., more preferably at 20 to 35° C. The specific solvent may be one or more solvent selected from dialkyl ether, cyclic ether, bicyclic ether, amide, (C$_1$-C$_4$)alkanol, toluene and xylene, more preferably, one or more solvent selected from dimethyl ether, diisopropyl ether, tetrahydrofuran, dioxane, dimethoxyethane, dimethylformamide, dimethylacetamide, toluene, xylene, ethanol and isopropanol.

When the 1,3-diazocycloalk-1-ene salt represented by Chemical Formula 2 is reacted with the metal-containing unsaturated olefin ligand under a specific condition, the saturated N-heterocyclic carbene-ligand metal complex derivative may be obtained in high yield. The carbene-ligand metal complex derivative may be synthesized, for example, according to Scheme 3, without being limited thereto:

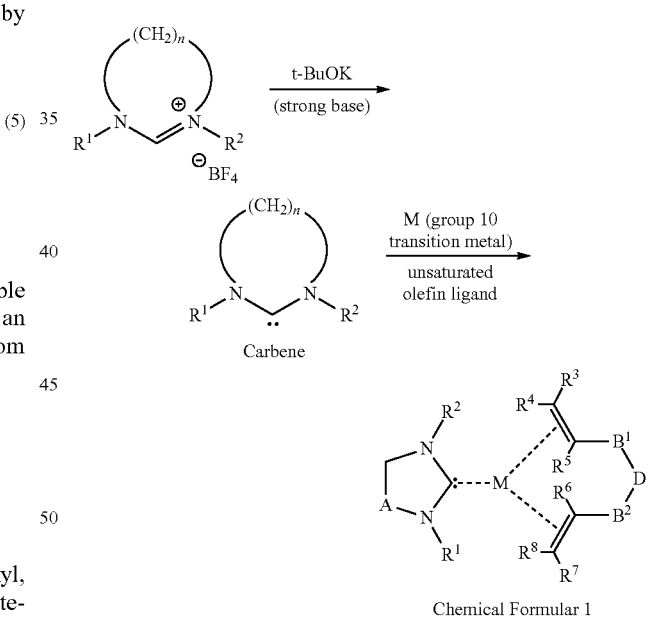

Chemical Formular 1

The carbene in Scheme 3 may be prepared from dehydrogenation an imidazolidine, triazolidine or pyrazolidine salt by the action of the base.

Preferably, the saturated N-heterocyclic carbene is used slightly in excess relative to the quantity of the transition metal. Accordingly, it is preferable to use 1 to 1.3 mol, more preferably 1 to 1.1 mol, of the saturated N-heterocyclic carbene based on 1 mol of the transition metal.

Thus prepared saturated N-heterocyclic carbene-ligand metal complex derivative of the present invention is appropriate to be used as a catalyst when preparing organosilane compounds by hydrosilylation.

Hereinafter, a method for preparing a silane compound using the saturated N-heterocyclic carbene-ligand metal complex derivative of the present invention will be described.

[Preparation of Silane Compound Using Saturated N-Heterocyclic Carbene-Ligand Metal Complex Derivative as Catalyst]

The present invention provides a method for preparing a method for preparing a silane compound by hydrosilylation in the presence of the saturated N-heterocyclic carbene-ligand metal complex represented by Chemical Formula 1:

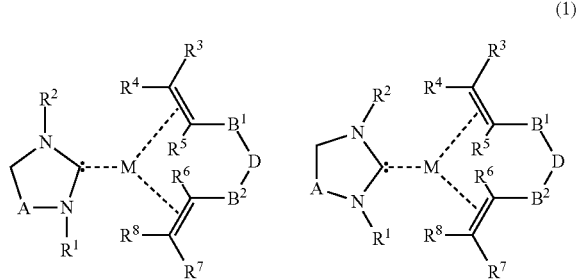

(1)

wherein the substituents of Chemical Formula 1 are the same as defined above.

As described earlier, the phrase "hydrosilylation reaction" refers to a reaction between a compound having one or more Si—H bonding unit(s) and an olefin (having double bond(s)), an acetylene derivative (having triple bond(s)) or an unsaturated hydrocarbon compound having both double and triple bonds to form C—Si bonds. Preferably, the olefin is $C_2$-$C_{40}$ linear, branched or cyclic aliphatic hydrocarbon having double bond(s), $C_2$-$C_{40}$ linear, branched or cyclic aliphatic hydrocarbon having double bond(s) and heteroatom(s), or $C_2$-$C_{40}$ aromatic hydrocarbon, and the acetylene derivative is $C_2$-$C_{40}$ linear, branched or cyclic aliphatic hydrocarbon having triple bond(s), or $C_2$-$C_{40}$ linear, branched or cyclic aliphatic hydrocarbon or $C_2$-$C_{40}$ aromatic hydrocarbon having triple bond(s) and heteroatom(s). Hereunder is given a more detailed description of the method for preparing a silane compound by hydrosilylation according to the present invention.

According to the present invention, a silane compound is prepared by hydrosilylating an unsaturated hydrocarbon compound with an organosilicon compound. More specifically, a silane compound is prepared by hydrosilylating an unsaturated hydrocarbon compound represented by Chemical Formula 6 with an organosilicon compound such as hydrosilane represented by Chemical Formula 7 or a siloxane polymer having a repeating unit represented by Chemical Formula 8 in the presence of the saturated N-heterocyclic carbene-ligand metal complex represented by Chemical Formula 1.

(6)

In Chemical Formula 6, $R^{10}$ is hydrogen or $C_1$-$C_5$ linear or branched alkyl; and $R^{11}$ is hydrogen, $C_1$-$C_5$ linear or branched alkyl, $C_3$-$C_{10}$ unsaturated hydrocarbon, $C_6$-$C_{10}$ aryl, $C_2$-$C_{10}$ carboxyl or

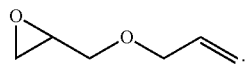

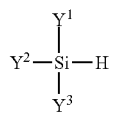

(7)

In Chemical Formula 7, $Y^1$ through $Y^3$ are identical to or different from one another, and each of $Y^1$ through $Y^3$ is hydrogen, $C_1$-$C_{10}$ linear or branched alkyl, $C_5$-$C_{10}$ cycloalkyl, $C_3$-$C_{10}$ unsaturated hydrocarbon, $C_6$-$C_{10}$ aryl, $C_1$-$C_{10}$ alkoxy, halogen or

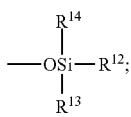

and $R^{12}$ through $R^{14}$ are identical to or different from one another, and each of $R^{12}$ through $R^{14}$ is hydrogen, $C_1$-$C_3$ alkyl or halogen. More preferably, $Y^1$ through $Y^3$ are identical to or different from one another, and each of $Y^1$ through $Y^3$ is hydrogen, $C_1$-$C_4$ linear or branched alkyl, $C_5$-$C_7$ cycloalkyl, phenyl, methylphenyl, $C_1$-$C_4$ alkoxy, —Cl or

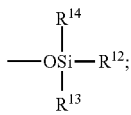

and $R^{12}$ through $R^{14}$ are identical to or different from one another, and each of $R^{12}$ through $R^{14}$ is hydrogen, methyl, ethyl or —Cl.

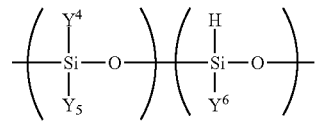

(8)

In Chemical Formula 8, $Y^4$ through $Y^6$ are identical to or different from one another, and each of $Y^4$ through $Y^6$ is hydrogen, $C_1$-$C_{10}$ linear or branched alkyl, $C_3$-$C_{10}$ cycloalkyl, $C_3$-$C_{10}$ unsaturated hydrocarbon, $C_6$-$C_{10}$ aryl, $C_1$-$C_{10}$ alkoxy or halogen. More preferably, $Y^4$ through $Y^6$ are identical to or different from one another, and each of $Y^4$ through $Y^6$ is hydrogen, $C_1$-$C_4$ linear or branched alkyl, $C_5$-$C_7$ cycloalkyl, phenyl, methylphenyl, $C_1$-$C_4$ alkoxy or —Cl. Preferably, the siloxane polymer having the repeat unit represented by Chemical Formula 8 has a weight average molecular weight of 300 to 10,000 g/mol.

In the method for preparing a silane compound according to the present invention, the hydrosilylation reaction may be performed in the presence or absence of a solvent. When the hydrosilylation reaction is performed in a solvent, the solvent may be an aliphatic hydrocarbon such as pentane, hexane, heptane, petroleum ether, etc.; an aromatic hydrocarbon such as benzene, toluene, xylene, etc.; a halogenated aliphatic or aromatic hydrocarbon such as tetrachloroethylene, chloroform, etc.; or an ether such as tetrahydrofuran, dioxane, etc.

The hydrosilylation reaction may be performed at 0 to 250° C., preferably at 0 to 100° C., more preferably at 0 to 70° C. The amount of the saturated N-heterocyclic carbene-ligand metal complex derivative which is used as the catalyst is not particularly limited.

The carbene-ligand metal complex derivative used as the catalyst may be determined so that the content of the transition metal included in the derivative is 1 to 1,000 ppm, preferably 1 to 100 ppm, more preferably 5 to 50 ppm.

MODE FOR INVENTION

The examples and experiments will now be described. The following examples and experiments are for illustrative purposes only and not intended to limit the scope of the present invention.

Preparation of N,N'-dialkyl-1,2-diaminoethane represented by $R^1$—NHCH$_2$CH$_2$NH—$R^2$

SYNTHESIS EXAMPLE 1-1

Preparation of N,N'-diisopropyl-1,2-diaminoethane ($R^1$=$R^2$=$^i$Pr)

All glasswares used in the synthesis were dried in an oven at 130° C. for about 15 hours and then cooled under dry nitrogen gas. Isopropylamine (32.2 g, 0.5447 mol) was added to a 250 mL 2-necked round-bottom flask equipped with a nitrogen gas inlet adapter and a reflux condenser. Then, 1,2-dibromoethane (14.5 g, 0.0772 mol) was added dropwisely at a rate of 1 mL/min.

When the temperature started to drop after a slight initial exothermic reaction, the mixture was heated and refluxed for 12 hours. After adding excess potassium oxide to saturation, followed by filtration under reduced pressure, the filtered solid was washed with diethyl ether. The resulting solution was transferred to a separatory funnel and the organic layer was extracted 3 times with diethyl ether. After drying the extracted organic layer by adding sodium sulfate, followed by filtration under reduced pressure, a solution free of diethyl ether was obtained. Distillation of the solution under reduced pressure yielded pure N,N'-diisopropyl-1,2-diaminoethane (7.6 g, yield=68%).

SYNTHESIS EXAMPLE 1-2

Preparation of N,N'-dicyclohexyl-1,2-diaminoethane ($R^1$=$R^2$=

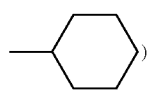

)

N,N'-Dicyclohexyl-1,2-diaminoethane (18.1 g, yield=83%) was prepared as in Synthesis Example 1-1, using cyclohexylamine (83.3 g, 0.840 mol) and 1,2-dibromoethane (19.3 g, 0.103 mol).

SYNTHESIS EXAMPLE 1-3

Preparation of N,N'-dimethyl-1,3-diaminopropane (CH$_3$—NHCH$_2$CH$_2$CH$_2$NH—CH$_3$)

N,N'-Dimethyl-1,3-Diaminopropane (6.1 g, Yield=56%) was Prepared as in Synthesis Example 1-1, using methylamine (26.4 g, 0.8500 mol) and 1,3-dibromopropane (21.5 g, 0.1065 mol).

Preparation of N,N'-dialkyl-1,3-imidazolium salt represented by

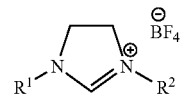

SYNTHESIS EXAMPLE 2-1

Preparation of N,N'-dimethyl-1,3-imidazolium salt ($R^1$=$R^2$=—CH$_3$)

N,N'-Dimethyl-1,2-diaminoethane (2.55 g, 29.2 mmol, Sigma-Aldrich), triethyl orthoformate (4.33 g, 28.9 mmol) and ammonium tetrafluoroborate (3.34 g, 31.8 mmol) were added to a 25 mL 2-necked round-bottom flask equipped with a nitrogen gas inlet tube and a cooling tube. The mixture was reacted by stirring for 18 hours while heating at 120° C. After stopping the stirring, the mixture was allowed to cool to room temperature. A white suspension was produced. After removing ethanol produced during the reaction, the suspension was dried under vacuum for 2 hours. A dry salt was obtained. The dry salt was dissolved in anhydrous ethanol and filtered and then the solvent was removed under reduced pressure. A white crystal was obtained. The white crystal was washed with excess diethyl ether and dried under vacuum for 12 hours while heating at 55° C. N,N'-dimethyl-1,3-imidazolium salt (4.72 g, yield=88%) was prepared.

SYNTHESIS EXAMPLE 2-2

Preparation of N,N'-diethyl-1,3-imidazolium salt ($R^1$=$R^2$=—CH$_2$CH$_3$)

N,N'-Diethyl-1,3-imidazolium salt (4.55 g, yield=98%) was prepared as in Synthesis Example 2-1, using N,N'-diethyl-1,2-diaminoethane (2.49 g, 21.4 mmol, Sigma-Aldrich), triethyl orthoformate (3.23 g, 21.5 mmol) and ammonium tetrafluoroborate (2.47 g, 23.6 mmol).

SYNTHESIS EXAMPLE 2-3

Preparation of N,N'-isopropyl-1,3-imidazolium salt ($R^1$=$R^2$=$^i$Pr)

N,N'-Isopropyl-1,3-imidazolium salt (4.85 g, yield=85%) was prepared as in Synthesis Example 2-1, using N,N'-isopropyl-1,2-diaminoethane (3.40 g, 23.6 mmol) prepared in Synthesis Example 1-1, triethyl orthoformate (3.49 g, 23.6 mmol) and ammonium tetrafluoroborate (2.59 g, 25.9 mmol).

SYNTHESIS EXAMPLE 2-4

Preparation of N,N'-cyclohexyl-1,3-imidazolium salt ($R^1$=$R^2$=

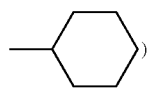
)

N,N'-Cyclohexyl-1,3-imidazolium salt 15.4 g, yield=98%) was prepared as in Synthesis Example 2-1, using N,N'-dicyclohexyl-1,2-diaminoethane (10.9 g, 48.6 mmol) prepared in Synthesis Example 1-2, triethyl orthoformate (7.2 g, 48.6 mmol) and ammonium tetrafluoroborate (5.60 g, 53.4 mmol).

SYNTHESIS EXAMPLE 2-5

Preparation of 1,3-dimethyl-pyrimidinium salt

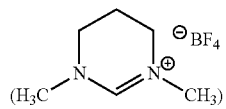

1,3-Dimethyl-pyrimidinium salt (2.90 g, yield=91%) was prepared as in Synthesis Example 2-1, using N,N'-dimethyl-1,3-diaminopropane (1.63 g, 16.0 mmol) prepared in Synthesis Example 1-3, triethyl orthoformate (2.59 g, 17.5 mmol) and ammonium tetrafluoroborate (1.84 g, 17.6 mmol).

Preparation of N,N'-dialkyl-1,3-imidazolin-2-ylidene carbene-platinum complex derivative

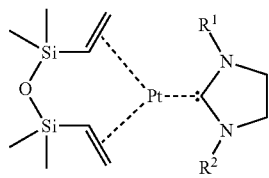

Example 1

N,N'-dimethyl-1,3-imidazolin-2-ylidene carbene-ligand platinum complex ($R^1$=$R^2$=—$CH_3$)

The N,N'-dimethyl-1,3-imidazolium salt prepared in Synthesis Example 2-1 (1,3-dimethyl-4,5-dihydroimidazolium tetrafluoroborate, 0.30 g, 1.56 mmol) was converted to a carbene by treating with potassium t-butoxide (1.0 M sol. in THF, 0.24 g, 2.06 mmol). Then, the carbene and a Karstedt solution (1.36 mmol) prepared according to U.S. Pat. No. 3,775,452 were added to a 100 mL 2-bulb round-bottom flask and then stirred for 6 hours to prepare a reaction mixture. After removing a salt produced during the stirring using Celite (Sigma Aldrich), the product was extracted by washing several times with toluene. After removing low-boiling-point compounds (including the toluene solvent) under reduced pressure, the solution was concentrated to 2 to 3 mL and crystallization was performed at 24° C. Thus produced crystal was washed with cold isopropanol (5 mL) and then 2 times with pentane (5 mL×2). Drying in vacuum yielded N,N'-dimethyl-1,3-imidazolin-2-ylidene carbene-platinum complex (0.56 g, yield=85%) as ivory powder.

$^1$H NMR: δ=0.29, 0.31 (s, 6H, $SiCH_3$), 1.70-1.97 (m, 4H) and 2.12-2.29 (m, 2H) (vinyl-protons), 2.95 (s, 6H, $NCH_3$), 3.67 (s, 4H, $NCH_2$).

Example 2

N,N'-diisopropyl-1,3-imidazolin-2-ylidene carbene-ligand platinum complex ($R^1$=$R^2$=$^i$Pr)

The N,N'-isopropyl-1,3-imidazolium salt prepared in Synthesis Example 2-3 (1,3-diisopropyl-4,5-dihydroimidazolium tetrafluoroborate, 0.51 g, 2.09 mmol) was converted to a carbene by treating with potassium t-butoxide (1.0 M sol. in THF, 0.32 g, 2.85 mmol). Then, N,N'-diisopropyl-1,3-imidazolin-2-ylidene carbene-ligand platinum complex (0.28 g, yield=85%) was prepared as in Example 1, using a Karstedt solution (1.93 mmol) prepared according to U.S. Pat. No. 3,775,452.

$^1$H NMR: δ=0.34, 0.30 (s, 6H, $SiCH_3$), 1.08 (s, 12H, $CH_3$) 1.68-1.92 (m, 4H) and 2.11-2.26 (m, 2H) (vinyl-protons), 3.56 (s, 4H, $NCH_2$), 2.95 (s, 6H, $NCH_3$), 4.37 (sept. 2H, CH).

Example 3

N,N'-dicyclohexyl-1,3-imidazolin-2-ylidene carbene-ligand platinum complex ($R^1$=$R^2$=

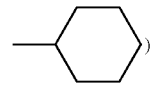
)

The N,N'-cyclohexyl-1,3-imidazolium salt prepared in Synthesis Example 2-4 (1,3-diisopropyl-4,5-dihydroimidazolium tetrafluoroborate, 0.34 g, 1.06 mmol) was converted to a carbene by treating with potassium t-butoxide (1.0 M sol. in THF, 0.16 g, 1.46 mmol). Then, N,N'-dicyclohexyl-1,3-imidazolin-2-ylidene carbene-ligand platinum complex (0.52 g, yield=88%) was prepared as in Example 1, using a Karstedt solution (0.95 mmol) prepared according to U.S. Pat. No. 3,775,452.

$^1$H NMR: δ=0.29, 0.31 (s, 6H, $SiCH_3$), 0.93-1.93 (m, 24H, overlapped peaks of vinyl-protons with c-hexyl-$CH_2$), 2.08-2.24 (m, 2H) (vinyl-protons), 3.55 (s, 4H, $NCH_2$), 3.84-4.01 (m, 2H, NCH).

Example 4

N,N'-dimethyl-1,3-pyrimidin-2-ylidene carbene-ligand platinum complex

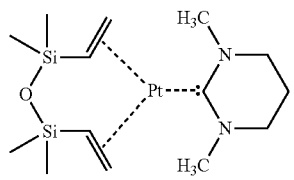

The 1,3-dimethyl-pyrimidinium salt prepared in Synthesis Example 2-5 (1,3-dimethyl-1,4,5,6-tetrahydropyrimidinium tetrafluoroborate, 0.42 g, 2.10 mmol) was converted to a carbene by treating with potassium t-butoxide (0.33 g, 2.90 mmol). Then, N,N'-dimethyl-1,3-pyrimidin-2-ylidene carbene-ligand platinum complex (0.80 g, yield=84%) was prepared as in Example 1, using a Karstedt solution (1.93 mmol) prepared according to U.S. Pat. No. 3,775,452.

$^1$H NMR: δ=0.33, 0.30 (s, 6H, SiCH$_3$), 1.66-1.90 (m, 4H) (vinyl-protons) and 2.05-2.35 (m, 4H, overlapped resonance of vinyl-protons with central-CH$_2$ of propylene unit), 3.09, 3.12 (s, 3H, NCH$_3$), 3.3.24 (t, J=8.0 Hz, 4H, NCH$_2$).

PREPARATION EXAMPLE 1

Preparation of Silane Compound by Hydrosilylation of Trichlorosilane and Styrene A catalyst described in Table 1 (0.0133 g, 2.77×10$^{-5}$ mol, 10$^{-3}$ mol per 1 mol of styrene) was added to a 25 mL 2-necked round-bottom flask equipped with a nitrogen gas inlet tube and a cooling tube. After adding trichlorosilane (8 g, 59.1 mmol) and dodecane (0.5 g, 2.9 mmol) as internal standard, the mixture was stirred in a water bath for 5 minutes. Then, styrene (3 g, 29.1 mmol) was added dropwisely at a rate of 1 mL/min using a syringe. Thereafter, the progress of reaction was monitored by gas chromatography.

The Karstedt catalyst of Comparative Example 1 was prepared according to U.S. Pat. No. 3,775,452. U-NHC$_5$-Me of Comparative Example 2 is

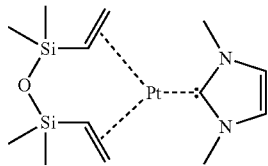

and was prepared according to Adv. Synth. Catal. 2004, 346, 1429. U-NHC$_5$-$^i$Pr of Comparative Example 3 is

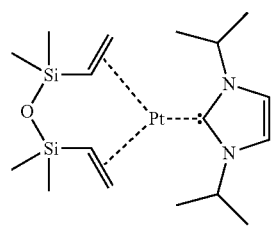

and was prepared according to Adv. Synth. Catal. 2004, 346, 1429.

The hydrosilylation reaction of Preparation Example 1 was performed according to Scheme 4. Reaction condition and yield of the produced silane compound are given in Table 2.

TABLE 1

| Catalyst | | Catalyst | |
|---|---|---|---|
| Ex. 1 | N,N'-Dimethyl-1,3-imidazolin-2-ylidene carbene-ligand platinum complex | Comp. Ex. 1 | Karstedt catalyst |
| Ex. 2 | N,N'-Diisopropyl-1,3-imidazolin-2-ylidene carbene-ligand platinum complex | Comp. Ex. 2 | U—NHC$_5$—Me |
| Ex. 3 | N,N'-Dicyclohexyl-1,3-imidazolin-2-ylidene carbene-ligand platinum complex | Comp. Ex. 3 | U—NHC$_5$—$^i$Pr |
| Ex. 4 | N,N'-Dimethyl-1,3-pyrimidin-2-ylidene carbene-ligand platinum complex | | |

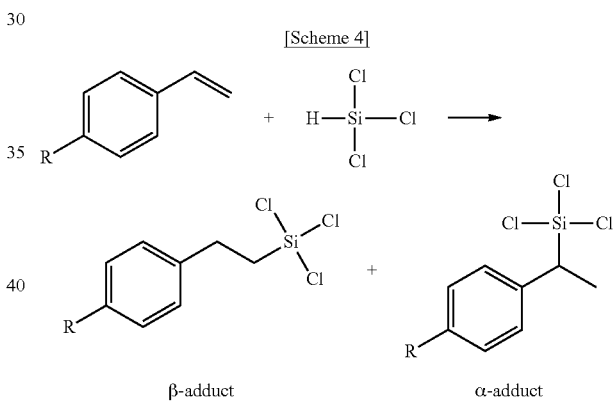

[Scheme 4]

TABLE 2

| | | Catalyst | | Reaction condition | | Remaining | Phenylethyl-trichlorosilane | |
|---|---|---|---|---|---|---|---|---|
| | R | Used catalyst | Amount (ppm) | Temp. (° C.) | Time (hr) | styrene (%) | Yield (%) | Isomer (β:α) |
| Comp. Ex. 1 | H | Karstedt | 100 | 16 | 0.5 | 5 | 69 | 66:34 |
| Comp. Ex. 3 | H | U—NHC$_5$—$^i$Pr | 100 | | 30 | 1 | 92 | 100:— |
| Ex. 1 | H | NHC$_5$—Me | 100 | | 3 | — | 90 | 95:5 |
| Ex. 2 | H | NHC$_5$—$^i$Pr | 100 | | 7 | — | 92 | 100:— |
| Comp. Ex. 1 | Cl | Karstedt | 100 | | 0.5 | 1 | 12 | 75:25 |
| Ex. 2 | Cl | NHC$_5$—$^i$Pr | 100 | | 12 | 4 | 81 | 100:— |
| Ex. 3 | Cl | NHC$_5$—$^c$Hx | 100 | | 12 | 1 | 82 | 100:— |
| Comp. Ex. 1 | H | Karstedt | 100 | 30 | 0.5 | 25 | 70 | 91:9 |
| Ex. 1 | H | NHC$_5$—Me | 100 | 30 | 4 | 23 | 72 | 100:— |

PREPARATION EXAMPLE 2

Preparation of Silane Compound by Hydrosilylation of Methyldichlorosilane and Styrene A catalyst described in Table 1 (50 ppm ($1.8 \times 10^{-6}$ mol) or 200 ppm ($7.2 \times 10^{-6}$ mol) of platinum included in the catalyst) was dissolved in xylene and added to a 25 mL 2-necked round-bottom flask equipped with a nitrogen gas inlet tube and a cooling tube. After adding dichloromethylsilane (3.98 g, 34.60 mmol) and dodecane (0.38 g, 2.2 mmol, used as internal standard for gas chromatography analysis), the mixture was stirred and then heated to 40° C. Then, styrene (3.0 g, 28.80 mmol) was added dropwisely at a rate of 1 mL/min using a syringe. Thereafter, the progress of reaction was monitored by gas chromatography.

The hydrosilylation reaction of Preparation Example 2 was performed according to Scheme 5. Reaction condition and yield of the produced silane compound are given in Table 3.

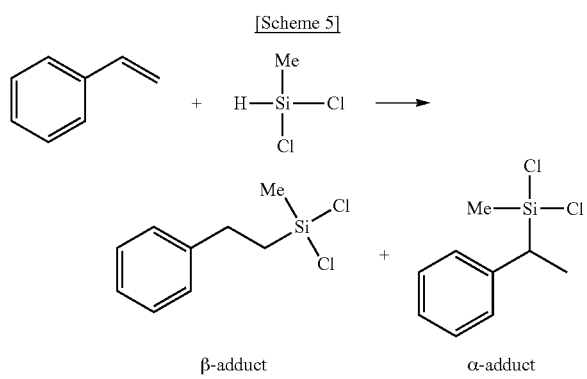

[Scheme 5]

β-adduct     α-adduct

The hydrosilylation reaction of Preparation Example 3 was performed according to Scheme 6. Reaction condition and yield of the produced silane compound are given in Table 4.

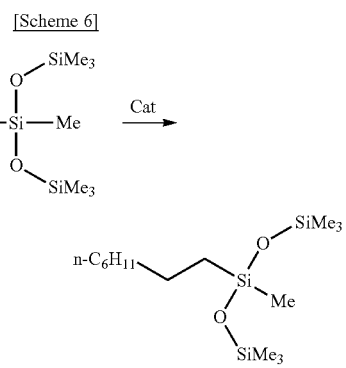

[Scheme 6]

TABLE 4

| Used catalyst | Reaction condition | | Remaining oct-1-ene | Product Yield |
|---|---|---|---|---|
| amount | Temp. (° C.) | Time (hr) | (%) | (%) |
| Comp. Ex. 1  5 ppm | 70 | 0.5 | 99 | trace |
| 10 ppm | 36 | 1 | 20 | 76 |
| Comp. Ex. 2  5 ppm | 70 | 6 | 1 | 90 |
| Ex. 1  5 ppm | 70 | 0.5 | — | 95 |
| 10 ppm | 36 | 1 | — | 96 |

TABLE 3

| | R | Used catalyst | Amount (ppm) | Temp. (° C.) | Time (hr) | Remaining styrene (%) | Yield (%) | Isomer (β:α) |
|---|---|---|---|---|---|---|---|---|
| | | | | Reaction condition | | | Phenylethyl-dichloromethylsilane | |
| Comp. Ex. 1 | H | Karstedt | 50 | 40 | 0.5 | 5 | 70 | 65:35 |
| Ex. 1 | H | NHC$_5$—Me | 50 | 40 | 4 | 4 | 73 | 93:7 |
| Ex. 2 | H | NHC$_5$—$^i$Pr | 200 | 40 | 8 | 15 | 67 | 100:— |

PREPARATION EXAMPLE 3

Preparation of Preparation of Silane Compound by Hydrosilylation of $(CH_3)_3Si$—O—$Si(CH_3)(H)$—OSi$(CH_3)_3$ and oct-1-ene A catalyst described in Table 1 (5 ppm ($1.9 \times 10^{-7}$ mol) or 10 ppm ($3.8 \times 10^{-7}$ mol) of platinum included in the catalyst) was dissolved in xylene and added to a 25 mL 2-necked round-bottom flask equipped with a nitrogen gas inlet tube and a cooling tube. After adding $(CH_3)_3SiO$—$Si(CH_3)(H)$—OSi$(CH_3)_3$ (4.96 g, 22.27 mmol) and dodecane (0.38 g, 2.2 mmol, used as internal standard for gas chromatography analysis), the mixture was stirred and then heated to 36° C. or 70° C. Then, oct-1-ene (2.5 g, 22.27 mmol) was added dropwisely at a rate of 1 mL/min using a syringe. Thereafter, the progress of reaction was monitored by gas chromatography.

PREPARATION EXAMPLE 4

Preparation of Preparation of Silane Compound by Hydrosilylation of $(CH_3)_3Si$—O—$Si(CH_3)(H)$—OSi$(CH_3)_3$ and Allyl Glycidyl Ether A catalyst described in Table 1 (15 ppm ($5.73 \times 10^{-7}$ mol) of platinum included in the catalyst) was dissolved in xylene and added to a 25 mL 2-necked round-bottom flask equipped with a nitrogen gas inlet tube and a cooling tube. After adding $(CH_3)_3SiO$—$Si(CH_3)(H)$—OSi$(CH_3)_3$ (4.96 g, 22.4 mmol) and dodecane (0.39 g, 2.2 mmol, used as internal standard for gas chromatography analysis), the mixture was stirred and then heated to 70° C. Then, allyl glycidyl ether

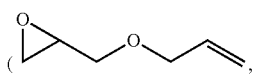

2.50 g, 22.2 mmol) was added dropwisely at a rate of 1 mL/min using a syringe. Thereafter, the progress of reaction was monitored by gas chromatography.

The hydrosilylation reaction of Preparation Example 4 was performed according to Scheme 7. Reaction condition and yield of the produced silane compound are given in Table 5.

[Scheme 7]

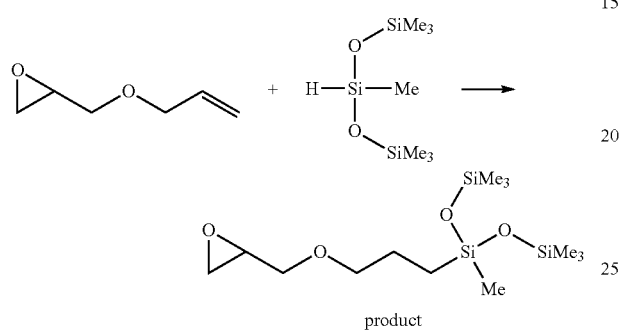

product

TABLE 5

| Used catalyst | Reaction condition | | | Remaining allyl glycidyl ether (%) | Product Yield (%) |
|---|---|---|---|---|---|
| | amount | Temp. (° C.) | Time (hr) | | |
| Comp. Ex. 1 | 15 ppm | 70 | 0.5 | 15 | 78 |
| Ex. 1 | 15 ppm | 70 | 0.5 | 16 | 79 |

PREPARATION EXAMPLE 5

Preparation of Preparation of Silane Compound by Hydrosilylation of Trimethoxysilane and Allyl Glycidyl Ether A catalyst described in Table 1 (20 ppm (1.2×10$^{-6}$ mol) of platinum included in the catalyst) was dissolved in xylene and added to a 25 mL 2-necked round-bottom flask equipped with a nitrogen gas inlet tube and a cooling tube. After adding trimethoxysilane (6.43 g, 52.6 mmol) and dodecane (0.5 g, 2.9 mmol) as internal standard, the mixture was stirred for 5 minutes under reflux. Then, allyl glycidyl ether (5.00 g, 43.8 mmol) was added dropwisely at a rate of 1 mL/min using a syringe. Thereafter, the progress of reaction was monitored by gas chromatography.

The hydrosilylation reaction of Preparation Example 5 was performed according to Scheme 8. Reaction condition and yield of the produced silane compound are given in Table 6.

[Scheme 8]

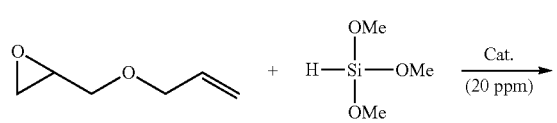

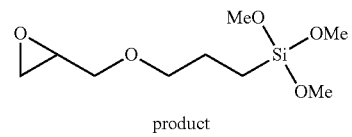

product

TABLE 6

| Used catalyst | Reaction condition | | | Remaining allyl glycidyl ether (%) | Product Yield (%) |
|---|---|---|---|---|---|
| | amount | Temp. (° C.) | Time (hr) | | |
| Comp. Ex. 1 | 20 ppm | reflux | 2 | 92 | 5 |
| Ex. 1 | 20 ppm | reflux | 2 | 16 | 82 |

PREPARATION EXAMPLE 6

Preparation of Preparation of Silane Compound by Hydrosilylation of Trichlorosilane and Phenylacetylene A catalyst described in Table 1 (100 ppm (4.0×10$^{-6}$ mol) of platinum included in the catalyst) was dissolved in xylene and added to a 25 mL 2-necked round-bottom flask equipped with a nitrogen gas inlet tube and a cooling tube. After adding trichlorosilane (4.76 g, 35.1 mmol) and dodecane (0.37 g, 2.2 mmol) as internal standard, the mixture was stirred for 5 minutes under reflux. Then, phenylacetylene (3.00 g, 29.4 mmol) was added dropwisely at a rate of 1 mL/min using a syringe. Thereafter, the progress of reaction was monitored by gas chromatography.

The hydrosilylation reaction of Preparation Example 6 was performed according to Scheme 9. Reaction condition and yield of the produced silane compound are given in Table 7.

[Scheme 9]

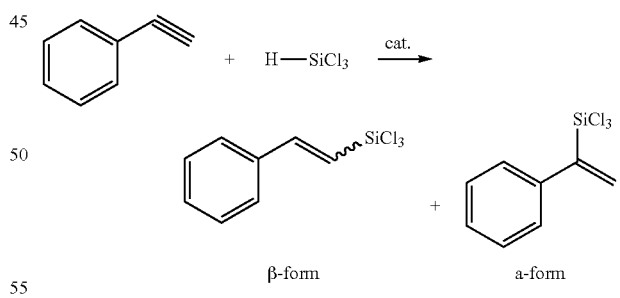

TABLE 7

| Used catalyst | Reaction condition | | | Remaining phenyl-acetylene (%) | Yield (%) | Isomer (β:α) |
|---|---|---|---|---|---|---|
| | amount | Temp. (° C.) | Time (hr) | | | |
| Comp. Ex. 1 | 100 ppm | 30 | 1 | 62 | 31 | 99:1 |
| Ex. 1 | 100 ppm | | 4 | 41 | 53 | 100:— |

PREPARATION EXAMPLE 7

Preparation of Preparation of Silane Compound by Hydrosilylation of $(CH_3)_3Si-O-Si(CH_3)(H)-OSi(CH_3)_3$ and 3-vinyl-7-oxabicyclo[4.1.0]Heptane

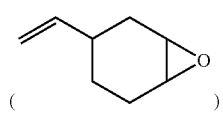
( )

A catalyst described in Table 1 (15 ppm ($6.4 \times 10^{-7}$ mol) of platinum included in the catalyst) was dissolved in xylene and added to a 25 mL 2-necked round-bottom flask equipped with a nitrogen gas inlet tube and a cooling tube. After adding $(CH_3)_3Si-O-Si(CH_3)(H)-OSi(CH_3)_3$ (5.38 g, 24.2 mmol) and dodecane (0.38 g, 2.2 mmol) as internal standard, the mixture was heated to 70° C. while stirring. Then, 3-vinyl-7-oxabicyclo[4.1.0]heptane

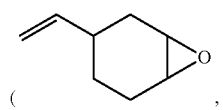
( , 3.00 g, 24.2 mmol) was added thereto dropwisely at a rate of 1 mL/min using a syringe. Thereafter, the progress of reaction was monitored by gas chromatography.

The hydrosilylation reaction of Preparation Example 7 was performed according to Scheme 10. Reaction condition and yield of the produced silane compound are given in Table 8.

[Scheme 10]

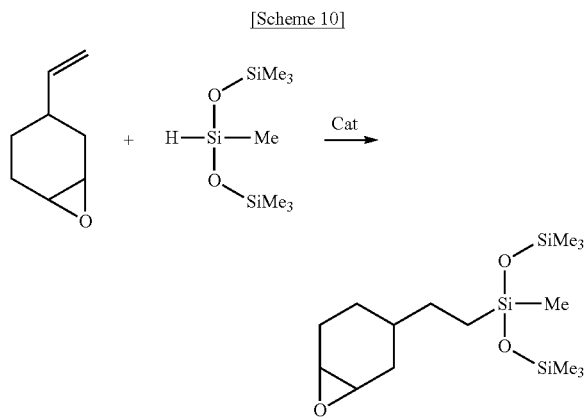

TABLE 8

| Used catalyst amount | Reaction condition | | Remaining 3-vinyl-7-oxabicyclo[4.1.0] heptane (%) | Yield (%) |
|---|---|---|---|---|
| (ppm) | Temp. (° C.) | Time (hr) | | |
| Comp. Ex. 1 | 15 | 70 | 4 | — | 92 |
| Ex. 1 | 15 | | 4 | — | 94 |

As demonstrated through Preparation Examples 1 to 7, when the saturated N-heterocyclic carbene-ligand metal complex derivatives of the present invention were used as catalyst in hydrosilylation reaction to prepare silane compounds, the silane compounds could be prepared with high regioselectivity (product selectivity) and high yield under low reaction temperature conditions.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A saturated N-heterocyclic carbene ligand metal complex represented by Chemical Formula 1:

(1)

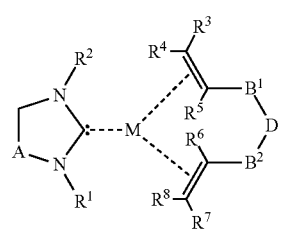

wherein

A is

$-(CHX^2)_{\overline{m}}-$;

$X^2$, $R^1$ and $R^2$ are identical to or different from one another, and each of $R^1$ and $R^2$ is $C_1$-$C_{18}$ linear or branched alkyl, $C_5$-$C_{18}$ cycloalkyl, $C_3$-$C_{18}$ unsaturated acyclic hydrocarbon, or phenyl, and $X^2$ is hydrogen, $C_1$-$C_3$ linear or branched alkyl, or phenyl;

M is a group 10 transition metal in the periodic table with oxidation state 0;

m is an integer from 1 to 2;

$B^1$ and $B^2$ are identical to or different from each other, and each of $B^1$ and $B^2$ is

$Si(X^3)_2$;

$X^3$ is $C_1$-$C_3$ linear or branched alkyl, or phenyl;

D is oxygen or

$-(CHX^2)_{\overline{l}}-$;

l is an integer from 1 to 4; and $R^3$, $R^4$, $R^5$, $R^6$, $R^7$, and $R^8$ are identical to or different from one another, and each of $R^3$, $R^4$, $R^5$, $R^6$, $R^7$, and $R^8$ is hydrogen, $C_1$-$C_3$ linear or branched alkyl, or phenyl.

2. The saturated N-heterocyclic carbene ligand metal complex derivative according to claim 1,
wherein
R$^1$ and R$^2$ are identical to or different from one another, and each of R$^1$ and R$^2$ is C$_1$-C$_{10}$ linear or branched alkyl, C$_5$-C$_{10}$ cycloalkyl, or phenyl; and
M is nickel, palladium or platinum.

3. A saturated N-heterocyclic carbene ligand metal complex represented by Chemical Formula 1:

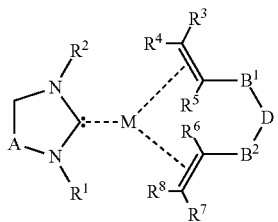

(1)

wherein
A is

m is an integer from 1 to 2;
X$^2$ is hydrogen;
each of R$^1$ and R$^2$ is C$_1$-C$_5$ linear or branched alkyl or C$_5$-C$_8$ cycloalkyl;
M is nickel, palladium or platinum;
B$^1$ and B$^2$ are identical to or different from each other, and each of B$^1$ and B$^2$ is

X$^3$ is C$_1$-C$_3$ linear or branched alkyl;
D is oxygen; and
each of R$^3$, R$^4$, R$^5$, R$^6$, R$^7$, and R$^8$ is hydrogen.

4. The saturated N-heterocyclic carbene ligand metal complex derivative according to claim 1, wherein M is platinum.

5. A method for preparing a saturated N-heterocyclic carbene-ligand metal complex represented by Chemical Formula 1, comprising:
reacting an unsaturated olefin ligand represented by Chemical Formula 3 with a group 10 (8B) transition metal in the periodic table with oxidation state 0 to prepare a metal-containing unsaturated olefin ligand;
treating a 1,3-diazocycloalk-1-ene salt represented by Chemical Formula 2 with a strong base to prepare a saturated N-heterocyclic carbene; and
reacting the saturated N-heterocyclic carbene with the metal-containing unsaturated olefin ligand at 0 to 70° C. in a specific solvent to synthesize a carbene-ligand metal complex derivative:

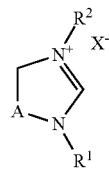

(2)

wherein
A is

X$^2$, R$^1$ and R$^2$ are identical to or different from one another, and each of R$^1$ and R$^2$ is C$_1$-C$_{18}$ linear or branched alkyl, C$_5$-C$_{18}$ cycloalkyl, C$_3$-C$_{18}$ unsaturated acyclic hydrocarbon or phenyl, and X$^2$ is hydrogen, C$_1$-C$_3$ linear or branched alkyl, or phenyl;
m is an integer from 1 to 2; and
X$^-$ is an anion derived from an organic or inorganic Brønsted acid, with pKa 0.01 to 6;

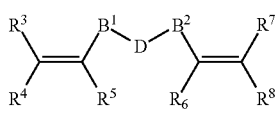

(3)

wherein
B$^1$ and B$^2$ are identical to or different from each other, and each of B$^1$ and B$^2$ is

X$^3$ is C$_1$-C$_3$ linear or branched alkyl, or phenyl;
D is oxygen or

l is an integer from 1 to 4; and
R$^3$, R$^4$, R$^5$, R$^6$, R$^7$, and R$^8$ are identical to or different from one another, and each of R$^3$, R$^4$, R$^5$, R$^6$, R$^7$, and R$^8$ is hydrogen, C$_1$-C$_3$ linear or branched alkyl, or phenyl; and

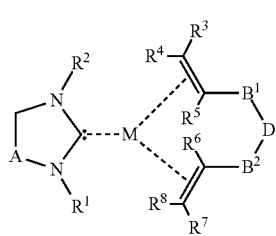

(1)

wherein
the substituents of Chemical Formula 1 are the same as in Chemical Formula 1 in claim 1.

6. The method for preparing a saturated N-heterocyclic carbene-ligand metal complex derivative according to claim 5, wherein the strong base is one or more selected from NaOH, NaOCH$_3$, KOH, KOCH$_2$(CH$_3$)$_2$, KOCH$_2$(CH$_3$)$_3$ and LiNHCH$_2$(CH$_3$)$_2$.

7. The method for preparing a saturated N-heterocyclic carbene-ligand metal complex derivative according to claim 5, wherein the metal-containing unsaturated olefin ligand is represented by Chemical Formula 5:

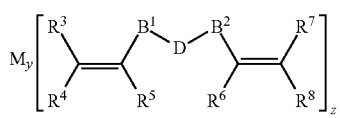
(5)

wherein
M is a group 10 transition metal in the periodic table with oxidation state 0;
y is an integer from 1 to 3;
z is an integer from 1 to 4;
B$^1$ and B$^2$ are identical to or different from each other, and each of B$^1$ and B$^2$ is

X$^3$ is C$_1$-C$_3$ linear or branched alkyl, or phenyl;
D is oxygen or

R$^3$ through R$^8$ are identical to or different from one another, and each of R$^3$ through R$^8$ is hydrogen, C$_1$-C$_3$ linear or branched alkyl, or phenyl; and
l is an integer from 1 to 4.

8. A method for preparing a silane compound hydrosilylating an unsaturated hydrocarbon compound with an organosilicon compound, wherein the catalyst used for said hydrosilylation is a saturated N-heterocyclic carbene-ligand metal complex derivative according to claim 1.

9. The method for preparing a silane compound according to claim 8, which comprises hydrosilylation of an unsaturated hydrocarbon compound represented by Chemical Formula 6 with an organosilicon compound represented by Chemical Formula 7 or Chemical Formula 8:

(6)

wherein
R$^{10}$ is hydrogen or C$_1$-C$_5$ linear or branched alkyl; and
R$^{11}$ is hydrogen, C$_1$-C$_5$ linear or branched alkyl, C$_3$-C$_{10}$ unsaturated hydrocarbon, C$_6$-C$_{10}$ aryl, C$_2$-C$_{10}$ carboxyl or

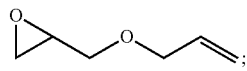

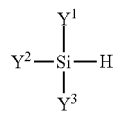
(7)

wherein
Y$^1$, Y$^2$ and Y$^3$ are identical to or different from one another, and each of Y$^1$, Y$^2$ and Y$^3$ is hydrogen, C$_1$-C$_{10}$ linear or branched alkyl, C$_5$-C$_{10}$ cycloalkyl, C$_3$-C$_{10}$ unsaturated hydrocarbon, C$_6$-C$_{10}$ aryl, C$_1$-C$_{10}$ alkoxy, halogen or

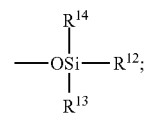

and
R$^{12}$, R$^{13}$ and R$^{14}$ are identical to or different from one another, and each of R$^{12}$, R$^{13}$ and R$^{14}$ is hydrogen, C$_1$-C$_3$ alkyl or halogen; and

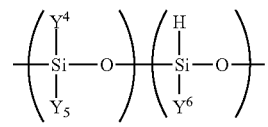
(8)

wherein
Y$^4$, Y$^5$ and Y$^6$ are identical to or different from one another, and each of Y$^4$, Y$^5$ and Y$^6$ is hydrogen, C$_1$-C$_{10}$ linear or branched alkyl, C$_5$-C$_{10}$ cycloalkyl, C$_3$-C$_{10}$ unsaturated hydrocarbon, C$_6$-C$_{10}$ aryl, C$_1$-C$_{10}$ alkoxy or halogen.

10. The method for preparing a silane compound according to claim 9,
wherein
Y$^1$, Y$^2$ and Y$^3$ are identical to or different from one another, and each of Y$^1$, Y$^2$ and Y$^3$ is hydrogen, C$_1$-C$_4$ linear or branched alkyl, C$_5$-C$_7$ cycloalkyl, phenyl, methylphenyl, C$_1$-C$_4$ alkoxy, —Cl or

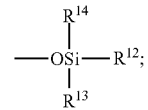

R$^{12}$, R$^{13}$ and R$^{14}$ are identical to or different from one another, and each of R$^{12}$, R$^{13}$ and R$^{14}$ is hydrogen, methyl, ethyl or —Cl; and
Y$^4$, Y$^5$ and Y$^6$ are identical to or different from one another, and each of Y$^4$, Y$^5$ and Y$^6$ is hydrogen, C$_1$-C$_4$ linear or branched alkyl, C$_5$-C$_7$ cycloalkyl, phenyl, methylphenyl, C$_1$-C$_4$ alkoxy or —Cl.

11. The method for preparing a silane compound according to claim 9, wherein the hydrosilylation reaction is performed in the presence or absence of a solvent.

12. The saturated N-heterocyclic carbene ligand metal complex derivative according to claim 2, wherein M is platinum.

13. The saturated N-heterocyclic carbene ligand metal complex derivative according to claim 3, wherein M is platinum.

14. A method for preparing a silane compound comprising hydrosilylating an unsaturated hydrocarbon compound with an organosilicon compound, wherein the catalyst used for said hydrosilylation is a saturated N-heterocyclic carbene-ligand metal complex derivative according to claim 2.

15. A method for preparing a silane compound comprising hydrosilylating an unsaturated hydrocarbon compound with an organosilicon compound, wherein the catalyst used for said hydrosilylation is a saturated N-heterocyclic carbene-ligand metal complex derivative according to claim 3.

16. A method of hydrosilation, wherein the method comprises reacting a compound containing an Si—H bond with a compound containing a double and/or triple bond in the presence of the N-heterocyclic carbene metal complex of claim 1 to form a reaction product, wherein the reaction product comprises one or more C—Si bonds.

* * * * *